(12) United States Patent
Wako

(10) Patent No.: US 6,699,181 B2
(45) Date of Patent: Mar. 2, 2004

(54) CONNECTOR DEVICE FOR ENDOSCOPE

(75) Inventor: Fumihide Wako, Saitama (JP)

(73) Assignee: Fuji Photo Optical Co., Ltd., Saitama (JP)

( * ) Notice: Subject to any disclaimer, the term of this patent is extended or adjusted under 35 U.S.C. 154(b) by 3 days.

(21) Appl. No.: 10/046,788

(22) Filed: Jan. 15, 2002

(65) Prior Publication Data

US 2002/0099265 A1 Jul. 25, 2002

(30) Foreign Application Priority Data

Jan. 19, 2001 (JP) ........................................ 2001-012166
Jan. 19, 2001 (JP) ........................................ 2001-012167

(51) Int. Cl.$^7$ ................................................ A61B 1/04
(52) U.S. Cl. ........................................ 600/132; 600/133
(58) Field of Search ................................ 600/132, 133, 600/112, 174

(56) References Cited

U.S. PATENT DOCUMENTS

| | | | | |
|---|---|---|---|---|
| 4,241,729 A | * | 12/1980 | Aoshiro | 600/133 |
| 4,261,345 A | * | 4/1981 | Yamaguchi | 600/132 |
| 4,414,608 A | * | 11/1983 | Furihata | 600/132 |
| 4,527,551 A | * | 7/1985 | Ishii | 600/132 |
| 4,538,593 A | * | 9/1985 | Ishii | 600/132 |
| 4,611,888 A | * | 9/1986 | Prenovitz et al. | 600/112 |
| 5,447,343 A | * | 9/1995 | Gajewski et al. | 600/133 |

FOREIGN PATENT DOCUMENTS

JP 09-066024 3/1997

\* cited by examiner

Primary Examiner—John Mulcahy
(74) Attorney, Agent, or Firm—Harness Dickey & Pierce P.L.C.

(57) ABSTRACT

The LG connector is composed of the proximal portion and the case body. The frame is supported by the proximal portion, and the universal cable and the control cable are fixed to this frame. Watertightness between the universal cable and the case body is maintained at an abutting surface which is orthogonal to the axis thereof, and watertightness between the control cable and the case body is maintained at the outer peripheral surface thereof. Thereby, it is possible to improve the efficiency of the assembly operation without deteriorating the watertightness of the LG connector. Also, the proximal portion is provided with the joint to be connected to the optical apparatus, and on this joint, the light guide bar is projectedly provided. Inside the proximal portion, the guide portion which guides the light guide to the insertion port of the light guide bar is projectedly formed. This guide portion enables the light guide to be easily installed without damaging the light guide.

16 Claims, 17 Drawing Sheets

CONNECTOR DEVICE FOR ENDOSCOPE

BACKGROUND OF THE INVENTION

1. Field of the Invention

The present invention relates to a connector device for an endoscope, and more particularly to a connector device for an endoscope provided at the distal end portion of a universal cable of an electronic endoscope, provided with a control cable to be connected to a processor, and a light guide bar to be connected to a light source device.

2. Description of the Related Art

At the distal end portion of an insertion portion of an endoscope, there is disposed an irradiation window, and inside the irradiation window, a light guide obtained by bundling extra-fine optical fibers is connected. The light guide is inserted from the insertion portion to an on-hand operating unit, and is further inserted into a universal cable which extends from the on-hand operating unit. Thus, the light guide is inserted into a light guide bar of a light guide connector (hereinafter, referred to as LG connector) provided at the distal end portion of the universal cable to be fixed. Therefore, the light guide bar is connected to a light source device, whereby an irradiation light from the light source device is transmitted through the light guide, and is irradiated toward a portion to be observed through an irradiation window. The electronic endoscope device picks up the portion to be observed with a solid state imaging device (e.g., charge-coupled device: CCD), and image-processes an electric signal to be outputted from the CCD by a processor to display an observed image on a monitor TV.

As shown in FIG. 14, a conventional LG connector is composed of a case body 1 having an aperture 1A, a lid 2 which covers the aperture 1A of the case body 1, and the like. On the case body 1, the light guide bar 3 which is connected to the light source device, is projectedly provided and an end portion of the universal cable 4 to be connected to the on-hand operating unit, and an end portion of a control cable 5 to be connected to the processor are fixed to the case body 1. This LG connector is assembled by fastening a screw (not shown) to a threaded hole 1B through a hole 2A to secure the lid 2 to the case body 1 by screws. Since the endoscope is dipped in a liquid medicine and is washed after use, it is necessary to reliably maintain the watertightness of the LG connector. Thus, between the case body 1 and the lid 2, there is provided packing 6 and the lid 2 is secured to the case body 1 by screws to thereby obtain the watertightness of the LG connector.

Since, however, the LG connector shown in FIG. 14 has a large aperture 1A of the case body 1, there has been a problem that it is difficult to reliably obtain the watertightness because of fitting error of the packing 6, manufacturing error of the case body 1 and the lid 2 and the like.

Japanese Patent Application Publication No. 9-66024 discloses a connector device for an endoscope which has solved the above-described problem. This connector device for an endoscope is, as shown in FIG. 15, composed of a proximal portion 7 equipped with a light guide bar 3, a case body 8 having an aperture 8A to be covered with the proximal portion 7, and the like. The aperture 8A is smaller than the aperture 1A of FIG. 14, and the aperture 8A is fitted in a groove formed at the proximal portion 7. Thus, the problem can be solved concerning the watertightness caused by the connector of FIG. 14. In this respect, a universal cable 4 and a control cable 5 are inserted into mounting holes 8B, 8C formed in a case body 8 respectively, and are connected to the proximal portion 7. This connector is assembled by causing, after the case body 8 is caused to slide on the proximal portion 7 side, mounting rings 9A, 9B to threadedly engage end portions of the universal cable 4 and the control cable 5 respectively.

In the connector device for an endoscope specified in Japanese Patent Application Publication No. 9-66024, however, when installing the case 8 to the proximal portion 7, it is necessary to seal two cables: the universal cable 4 and the control cable 5, and the case body 8, but this sealing structure has not been disclosed.

Also, as shown in FIG. 17, a light guide bar 101 is projectedly provided on a case 102 for the LG connector. The light guide bar 101 is formed in a cylindrical shape, and at the distal end portion, there is disposed an LG window glass 103. A light guide 104 is pushed into the light guide bar 101 through an insertion port 105, and after inserted to the position of the LG window glass 103, is fixed by a setscrew 106.

Since, however, the insertion port 105 of the light guide bar 101 is located at a back position difficult to be recognized, the light guide 104 had to be pushed in by touch. For this reason, the conventional LG connector has a defect that it takes time to install the light guide 104.

Also, when the distal end portion of the light guide 104 is not smoothly inserted into the light guide bar 101, but strikes against the case 102, there is a fear of the light guide 104 being damaged. When the light guide 104 has been damaged, there arises a disadvantage that a quantity of light of the irradiation light to be irradiated through the irradiation window decreases. Also, in an endoscope in which one light guide 104 is branched off into two to irradiate through two irradiation windows, the damage to the light guide 104 also causes a disadvantage that quantity of light of the irradiation light to be irradiated through these two irradiation windows will get out of balance.

SUMMARY OF THE INVENTION

The present invention has been developed in view of the above-described circumstances, and has as its object the provision of a connector device for an endoscope capable of obtaining the watertightness between the case body of the connector device and the cable, and improving the assembly workability.

Also, it is an object of the present invention to provide a connector device for an endoscope capable of easily installing the light guide to the light guide bar without damaging the light guide.

In order to achieve the above-described object, the present invention is directed to a connector device for an endoscope, wherein: a first cable to be connected to an endoscope on-hand operating unit and a second cable to be connected to a controller which processes a signal are coupled on a first side of a proximal portion of the connector device; a light guide bar to be coupled to a light source device is provided on a second side of the proximal portion of the connector device; the first side of the proximal portion is watertightly sealed with a case body which has an insertion port of the first cable and an insertion port of the second cable; the case body and one of the first cable and the second cable are sealed by a first sealing member provided on an outer peripheral surface of the one of the first cable and the second cable; and the case body and the other one of the first cable and the second cable are sealed by a second sealing member provided on a surface orthogonal to an axis of the other one of the first cable and the second cable.

According to the present invention, the structure is arranged such that of two cables: the first cable and the second cable, one cable and the case body are sealed by the outer peripheral surface of the one cable, and the other cable and the case body are sealed by a surface orthogonal to the axis thereof. With such a structure, the assembly property can be improved without deteriorating the watertightness.

Also, in order to achieve the above-described object, the present invention is directed to a connector device for an endoscope, having a light guide bar provided at the end portion of the endoscope cable, which is connected to the light source device, constructed such that the end portion of the light guide inserted into the endoscope cable is inserted into the light guide bar, wherein the connector device is provided with a guide member which guides the light guide to the light guide bar.

According to the present invention, since the guide member has been provided, the light guide can be caused to be smoothly inserted into the light guide bar. Therefore, when inserting the light guide into the light guide bar, the light guide can be prevented from being damaged.

BRIEF DESCRIPTION OF THE DRAWINGS

The nature of this invention, as well as other objects and advantages thereof, will be explained in the following with reference to the accompanying drawings, in which like reference characters designate the same or similar parts throughout the figures and wherein.

DETAILED DESCRIPTION OF THE PREFERRED EMBODIMENTS

Hereunder a preferred embodiment will be described in detail for a structure of a connector device for an endoscope according to preferred embodiments of the present invention in accordance with the accompanied drawings.

Figure 1:
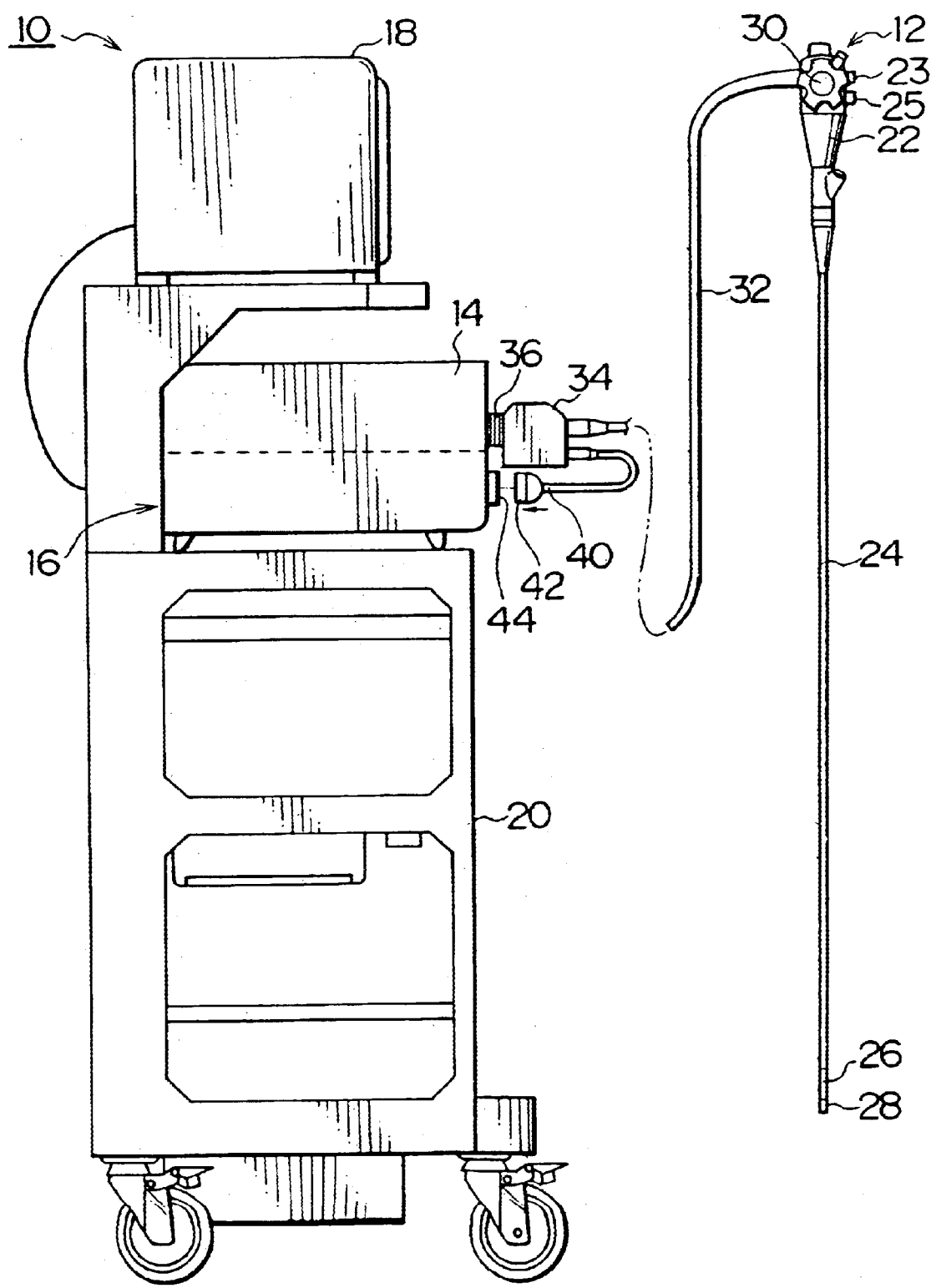
FIG. 1 is a general block diagram showing an electronic endoscope device using a connector device for the endoscope according to the present invention.

FIG. 1 is a general block diagram showing an electronic endoscope device 10 to which a connector device for an endoscope according to the present invention has been mounted.

An electronic endoscope device 10 shown in FIG. 1 comprises an electronic endoscope 12, a processor (corresponds to a controller) 16 with a built-in light source device 14, a monitor TV 18 and the like. These processor 16 and monitor TV 18 are housed in a rack 20 capable of freely traveling.

The electronic endoscope 12 has an on-hand operating unit 22, and to this on-hand operating unit 22, an insertion portion 24 which is inserted into a body is connected. At the distal end of the insertion portion 24, there is provided a distal end assembly 28 through a crook 26. The crook 26 is crook-controlled from a distance by rotating a knob 30 provided at the operating unit 22. At the end surface of the distal end assembly 28, there are disposed an object lens (not shown), an irradiation window and the like, and inside the object lens, there is provided a solid state imaging device (CCD).

From the on-hand operating unit 22, a universal cable (corresponds to the first cable) 32 extends. In the universal cable 32, there are inserted a light guide which transmits an irradiation light from the light source device 14 to the irradiation window at the distal end assembly 28, a signal cable which transmits an electric signal from the CCD, and the like. The light guide is connected to a connector 36 on the light source device 14 side through the LG connector 34. Thereby, an irradiation light from the light source device 14 is transmitted through the light guide to be irradiated to the portion to be observed through the irradiation window at the distal end assembly 28. On the other hand, a signal cable is inserted into a control cable (corresponds to the second cable) 40 extending from the LG connector 34, and is connected to a connector 44 of the processor 16 through an electric connector 42. Thereby, the electric signal to be outputted from the CCD is transmitted to the processor 16.

Figure 2:
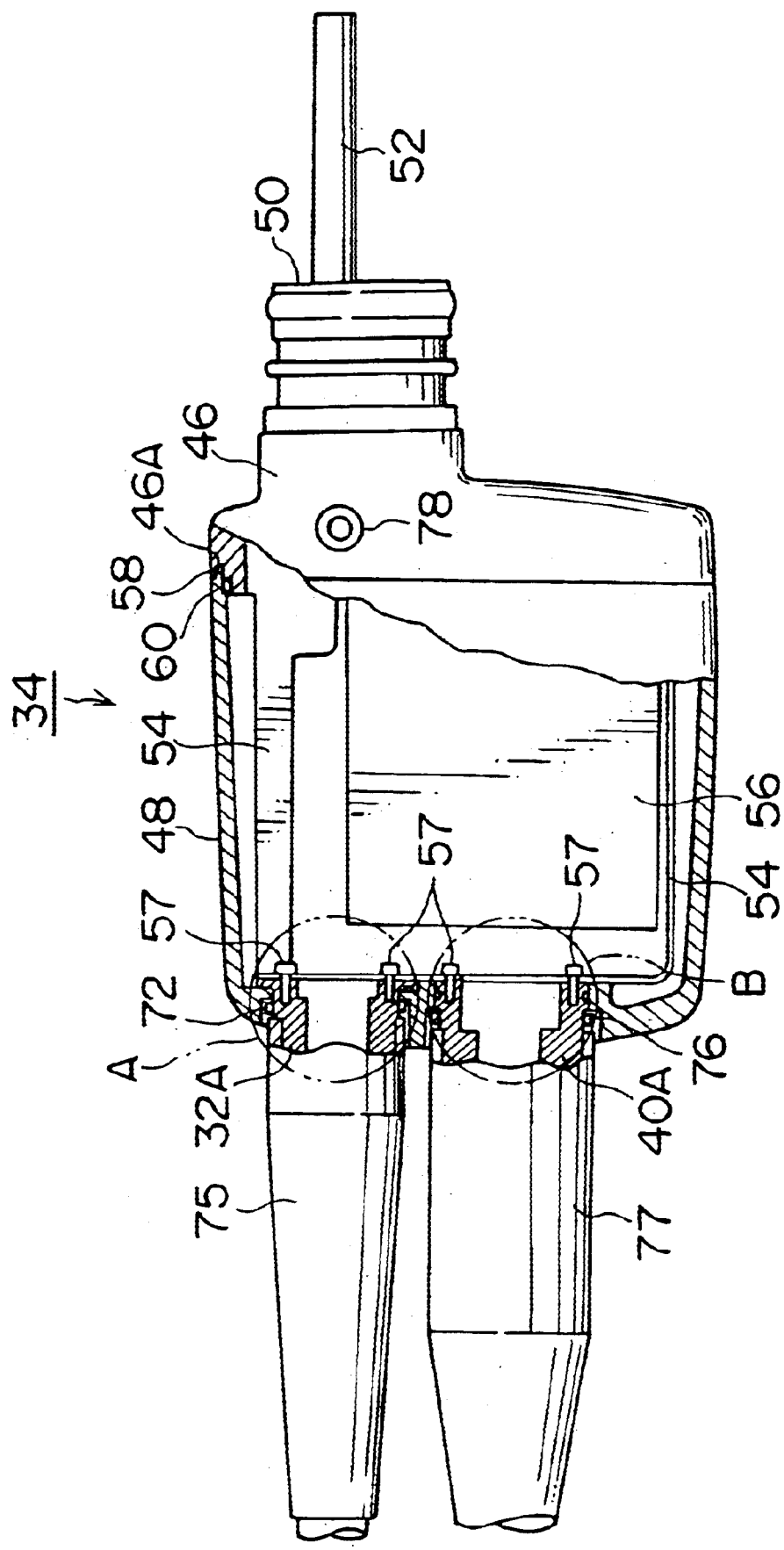
FIG. 2 is a side view showing an LG connector.
Figure 3:
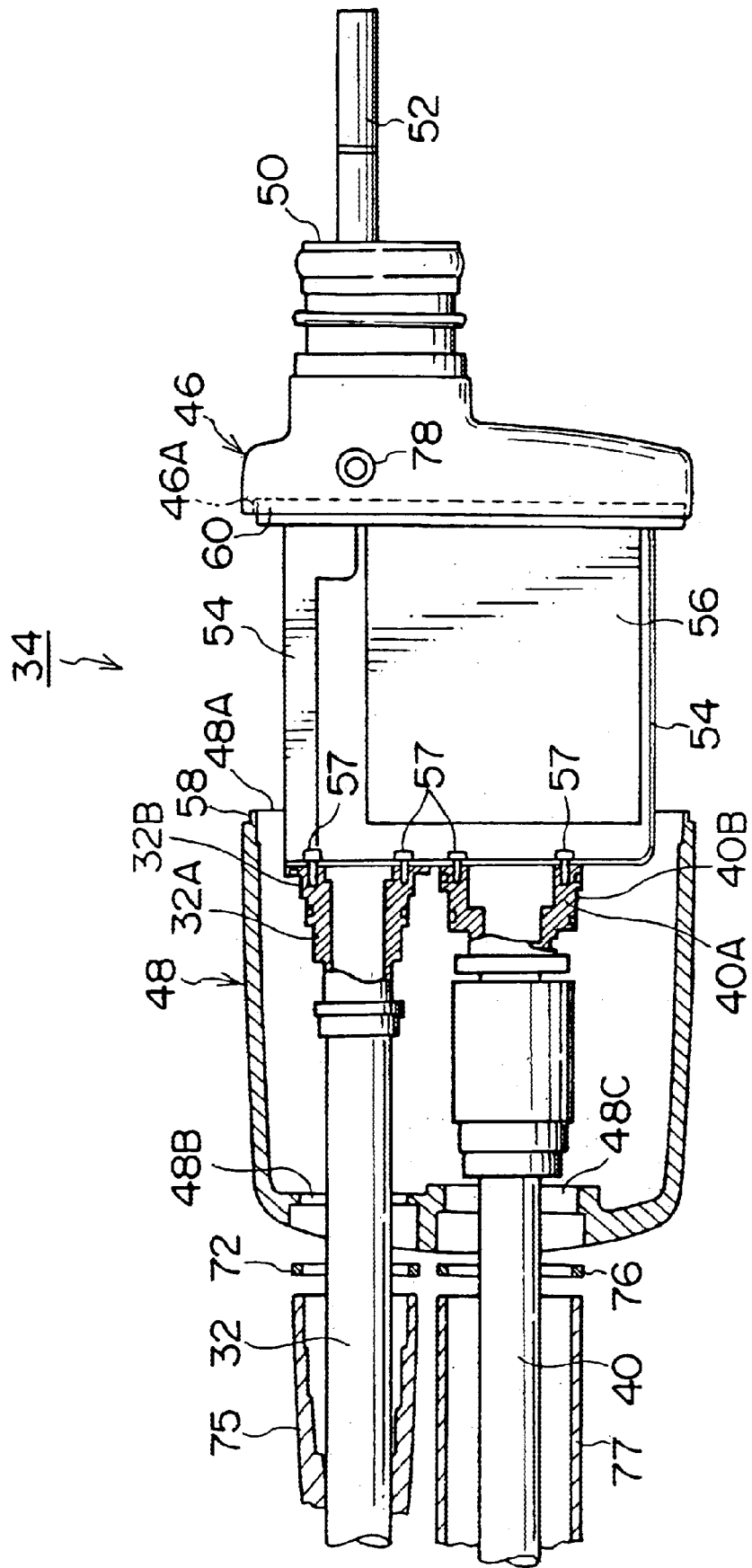
FIG. 3 is an assembly view showing the LG connector.

As shown in FIGS. 2 and 3, the LG connector 34 is formed in a substantially rectangular parallelepiped by a proximal portion 46 and a case body 48 which are made of synthetic resin. The proximal portion 46 is provided with a joint 50 to be connected to the connector 36 of the light source device 14, and on this joint 50, a light guide bar 52 is projectedly provided. Also, at the proximal portion 46, a frame 54 is supported at a side opposite to the joint 50. Within the frame 54, there is mounted a circuit board 56 on which a signal processing circuit for processing an electric signal into a video signal has been provided. Also, onto the frame 54, a distal end portion 32A of the universal cable 32 and a distal end portion 40A of the control cable 40 are fixed by screws 57.

On the other hand, the case body 48 has housing space therein which houses the frame 54, and is formed with an aperture 48A on the proximal portion 46 side. On a surface opposite to the aperture 48A, there are formed a mounting hole 48B for the universal cable 32 and a mounting hole 48C for the control cable 40. On the periphery of the aperture 48A of the case body 48, a protruding ridge portion 58 is formed in a substantially ring shape, and this protruding ridge portion 58 is fitted in a receding ridge groove 46A of the proximal portion 46. Inside the receding ridge groove 46A, there is disposed an O-ring 60, and the proximal portion 46 and the case body 48 is sealed through the use of the O-ring 60.

The case body 48 is fixed by causing, after the protruding ridge portion 58 is fitted into the receding ridge groove 46A, a mounting ring 72 to threadedly engage the distal end portion 32A of the universal cable 32 and a mounting ring 76 to threadedly engage the distal end portion 40A of the control cable 40. After the case body 48 is fixed, a cover 75 is fitted over the distal end portion 32A of the universal cable 32, and a cover 77 is fitted over the distal end portion 40A of the control cable 40.

Figure 4:
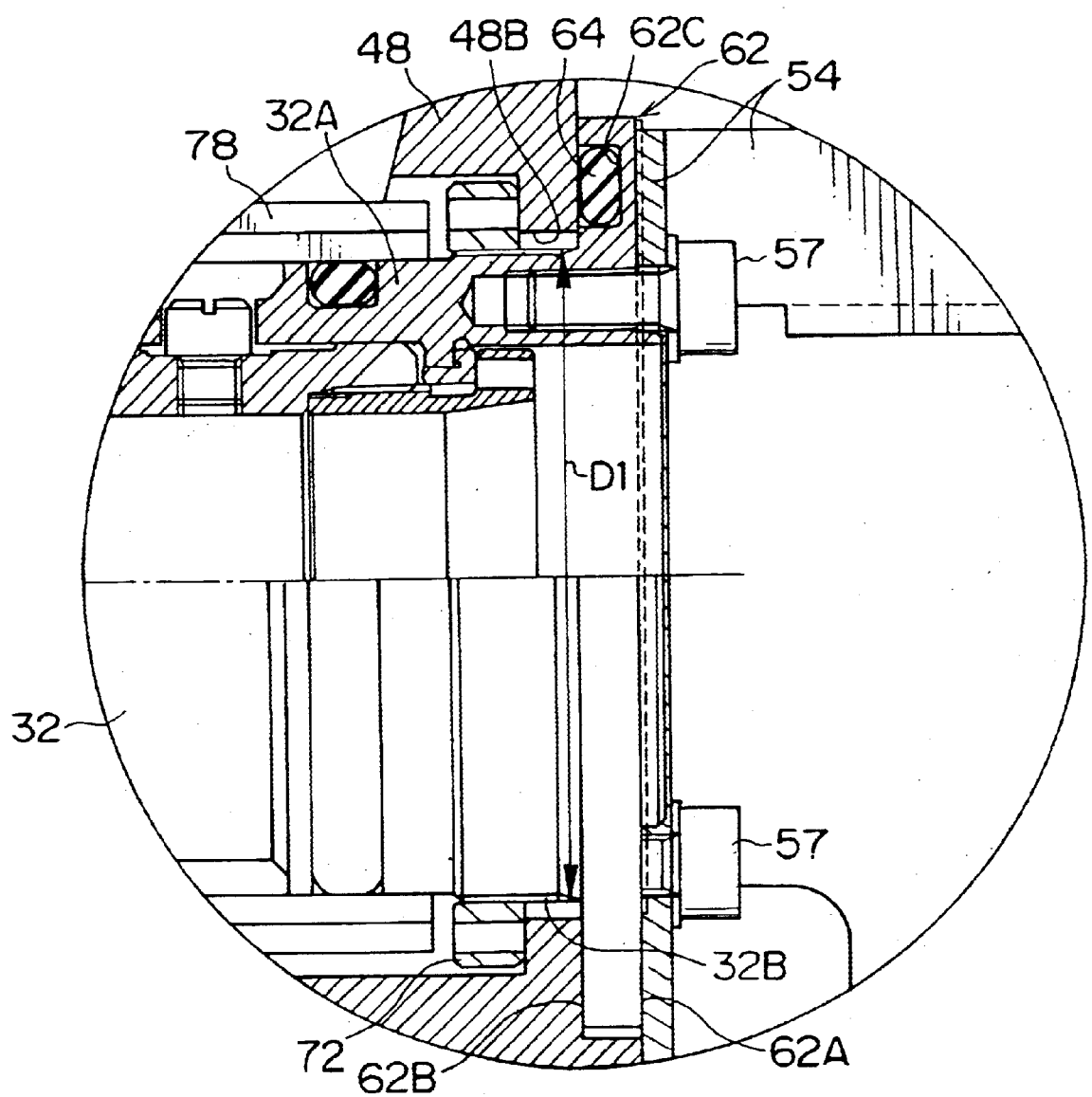
FIG. 4 is an enlarged view showing a portion A of FIG. 2.

As shown in FIG. 4, the universal cable 32 is formed such that the outer diameter D1 of the distal end portion 32A is somewhat smaller than the inner diameter of the mounting hole 48B of the case body 48. Therefore, when the distal end portion 32A is inserted into the mounting hole 48B, some gap is formed between the distal end portion 32A and the mounting hole 48.

On the end surface of the distal end portion 32A, there is formed a flange 62. In the flange 62, the distal end surface 62A is coupled to the frame 54, and at a side opposite to the distal end surface 62A, there is formed an abutting surface 62B which abuts against the case body 48. When the protruding ridge portion 58 of the case body 48 is fitted into the receding ridge groove 46A of the proximal portion 46, the abutting surface 62B is adapted to abut against the case body 48. On the abutting surface 62B, there is formed a ring-shaped groove 62C, and an O-ring (corresponds to the second sealing member) 64 is fitted in this groove 62C. The flange 62 and the case body 48 are sealed by this O-ring 64. More specifically, the sealing structure between the universal cable 32 and the case body 48 is provided on a surface orthogonal to the axis of the universal cable 32 and is pressed in the axial direction of the universal cable 32 to thereby secure the sealability.

Figure 5:
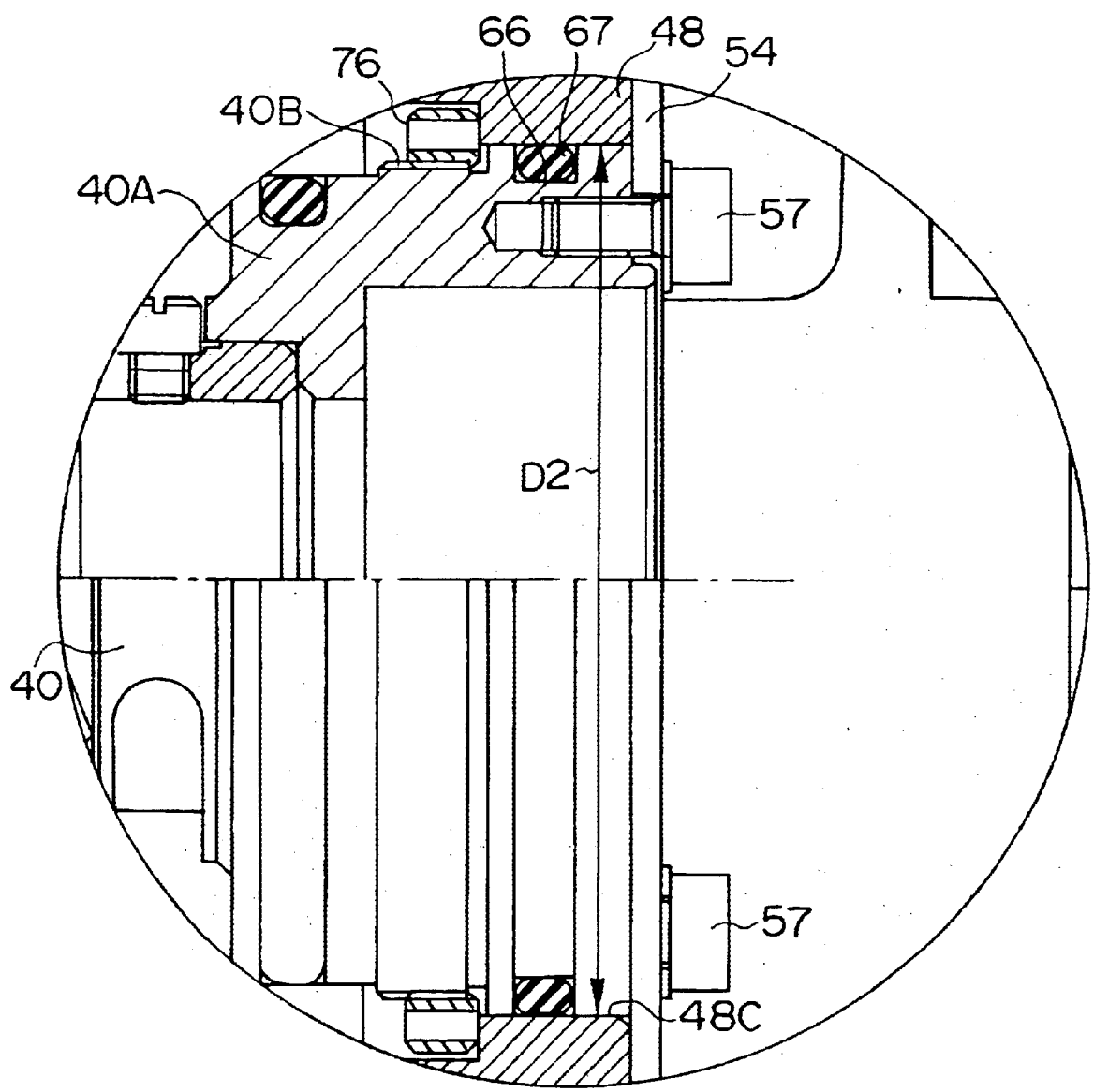
FIG. 5 is an enlarged view showing a portion B of FIG. 2.

On the other hand, the control cable 40 is, as shown in FIG. 5, formed such that the outer diameter D2 of the distal end portion 40A becomes the substantially same diameter as the diameter of the mounting hole 48C, and the distal end portion 40A is fitted in the mounting hole 48C. On the outer peripheral surface of the distal end portion 40A, a groove 66 is formed, and an O-ring (corresponds to the first sealing member) 67 is fitted into the groove 66. The distal end portion 40A and the mounting hole 48C are sealed with this O-ring 67. More specifically, in the control cable 40, the sealing structure with the case body 48 is provided on the outer peripheral surface of the control cable 40, and is pressed in a direction orthogonal to the axial direction of the control cable 40 to thereby secure the sealability.

Figure 6:
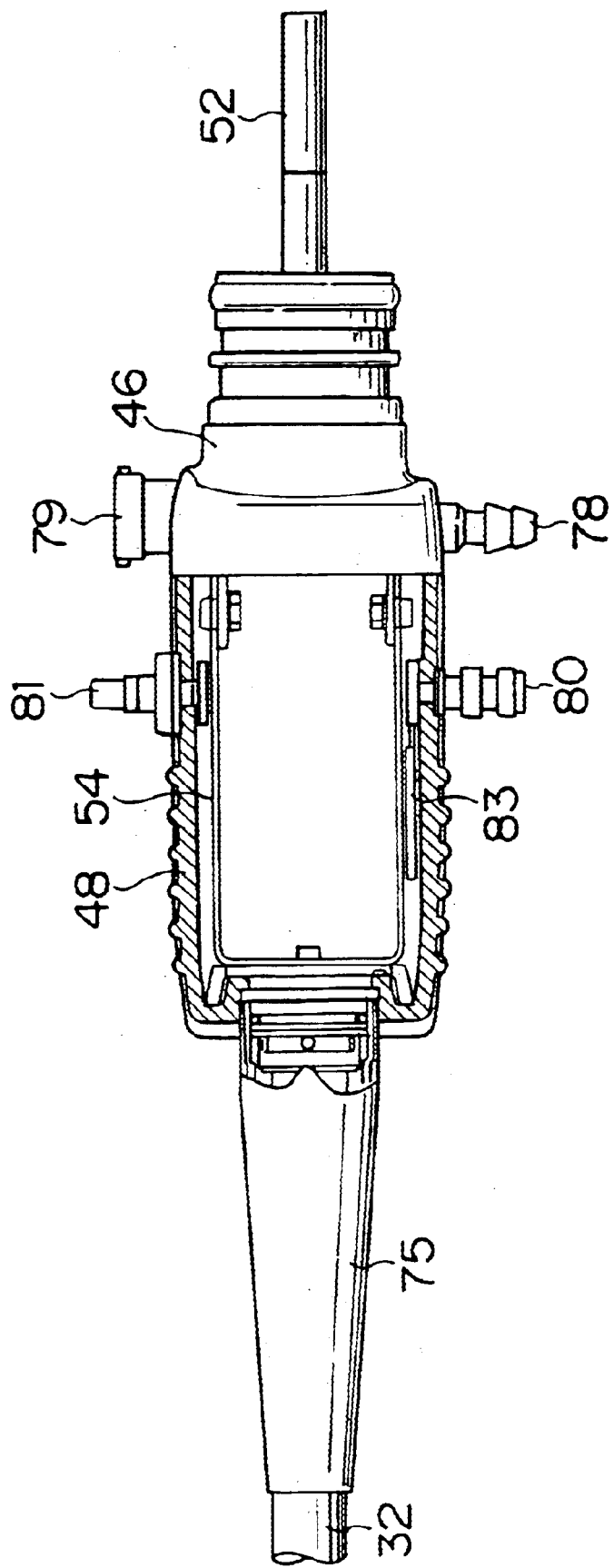
FIG. 6 is a plan view showing the LG connector.

As shown in FIG. 6, the LG connector 34 is provided with a suction piping tool 78, an air/water piping tool 79, a S-terminal 80, and a breathing connector 81. The suction piping tool 78 and the air/water piping tool 79 are disposed at the proximal portion 46, and the S-terminal 80 and the breathing connector 81 are disposed on the case body 48.

The suction piping tool 78 is a connector which connects a tube from a suction apparatus (not shown), and a suction tube (not shown) is connected inside the proximal portion 46. The suction tube is inserted into the universal cable 32, and is connected to a suction port (not shown) of the distal end assembly 28 through a suction valve 23 provided at the on-hand operating unit 22 of FIG. 1. Thus, by operating the suction valve 23, a morbid portion and the like which have been cut off can be sucked from the suction port.

The air/water piping tool 79 is a connector which connects a tube from a water supply tank (not shown), and inside the proximal portion 46, an air/water tube (not shown) is connected. The air/water tube is inserted into the universal cable 32, and is connected to an air/water port formed at the distal end assembly 28 through an air/water valve 25 provided at the on-hand operating unit 22 of FIG. 1. Thus, by operating the air/water valve 25, water from an air or water tank is emitted from the air/water port.

The S-terminal 80 is a terminal to connect a S-cord when using an electric surgical operation apparatus (electric surgical knife)(not shown), and inside the case body 48, an electric lead 83 is connected.

The breathing connector 81 is a connector to connect an airtight tester when inspecting the electronic endoscope 12 for watertightness.

Figure 16:
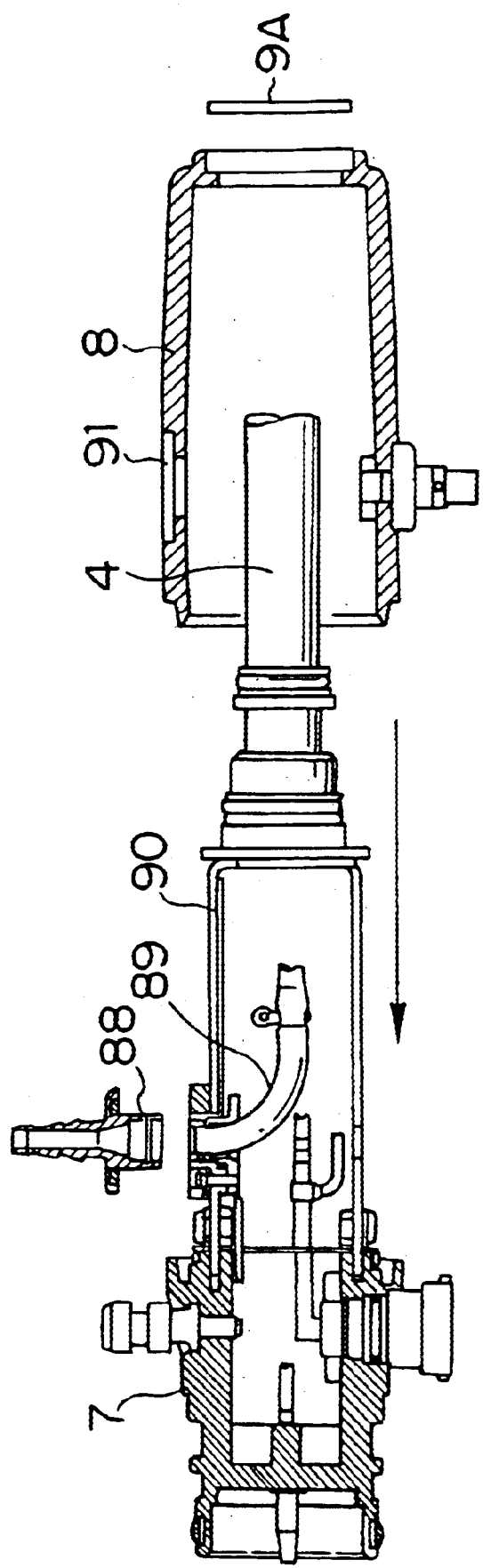
FIG. 16 is a plan view showing the conventional connector for the endoscope.
Figure 17:
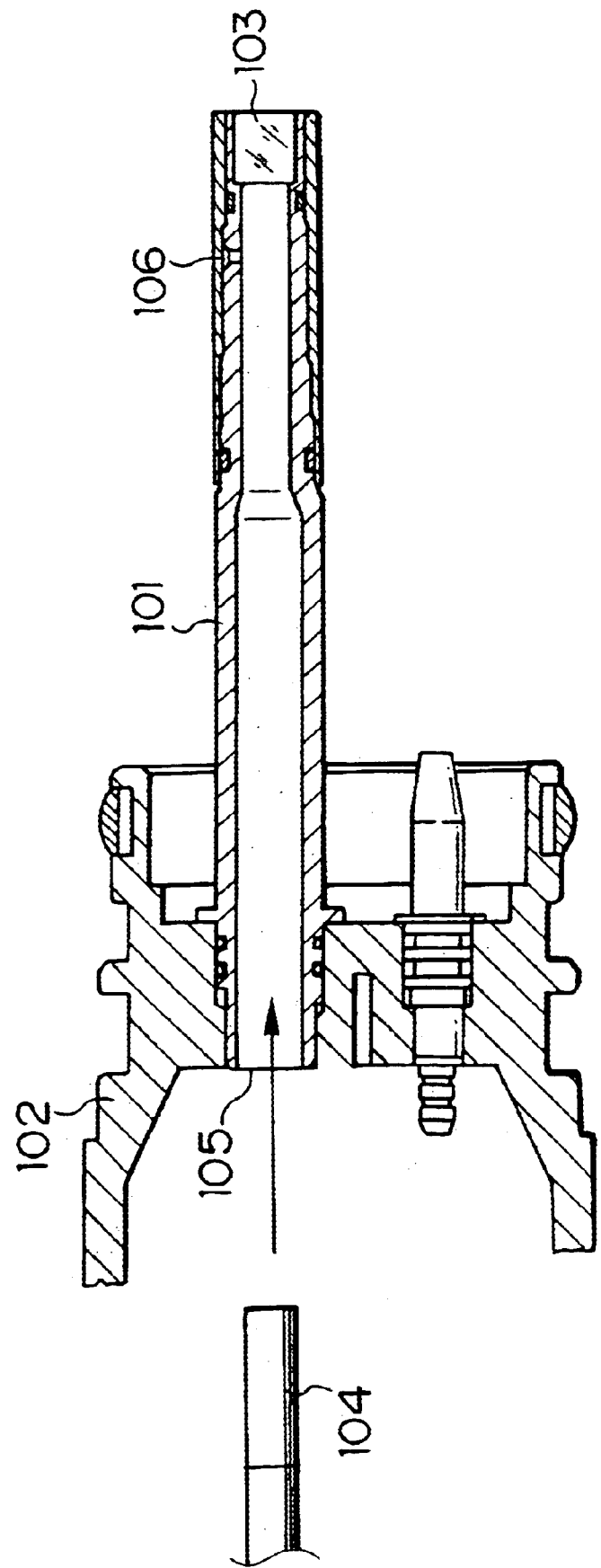
FIG. 17 is a view showing the structure of the conventional LG connector.

When the suction piping tool 78 is disposed on the proximal portion 46 as described above, the assembly property of the LG connector 34 can be improved. More specifically, when the suction piping tool 88 is disposed on the case body 8 side as shown in FIG. 16, a connecting pipe 89 for connecting to the tube is fixed to a frame 90, thereafter the case body 8 is caused to slide on the proximal portion 7 side, the suction piping tool 88 is inserted from the mounting hole 91, and is connected to a connecting pipe 89 to fix to the case body 8. In this case, alignment between a fixed position of the connecting pipe 89 and the mounting hole 91 of the case body 8 becomes complicated. Since, however, the LG connector 34 is constructed such that the suction piping tool 78 is disposed on the proximal portion 46 side and is directly connected to the connecting pipe 89, it becomes unnecessary to align with the suction piping tool 78, thus improving the assembly property of the LG connector 34.

Next, the description will be made of an assembly method for the LG connector 34.

First, as shown in FIG. 3, the universal cable 32 which has been inserted into the cover 75 and the mounting ring 72 is inserted into the mounting hole 48B of the case body 48, and the distal end portion 32A is fixed to the frame 54. Similarly, the control cable 40 which has been inserted into the cover 77 and the mounting ring 76 is inserted into the mounting hole 48C of the case body 48, and the distal end portion 40A is fixed to the frame 54.

Next, after the termination of various operations such as an operation for mounting the circuit board 56 and a wiring operation, the case body 48 is caused to slide on the proximal portion 46 side. Thus, the distal end portion 32A of the universal cable 32 is loosely fitted in the mounting hole 48B of the case body 48, and the distal end portion 40A of the control cable 40 is fitted into the mounting hole 48C of the case body 48.

Next, the protruding ridge portion 58 of the case body 48 is caused to fit into the receding ridge groove 46A of the proximal portion 46. Thus, the mounting ring 72 is caused to threadedly engage the male screw 32B at the distal end portion 32A, and the mounting ring 76 is caused to threadedly engage the male screw 40B at the distal end portion 40A to thereby fix the case body 48. Then, the cover 75 is caused to slide on the case body 48 side along the universal cable 32 to fit into the distal end portion 32A, and the cover 77 is caused to slide on the case body 48 side along the control cable 40 to fit into the distal end portion 40A. Thereby, the assembly operation of the LG connector 34 is completed.

Next, in comparison with the connector shown in FIGS. 7 and 8, the description will be made of an operation of the LG connector 34 constructed as described above.

Figure 7:
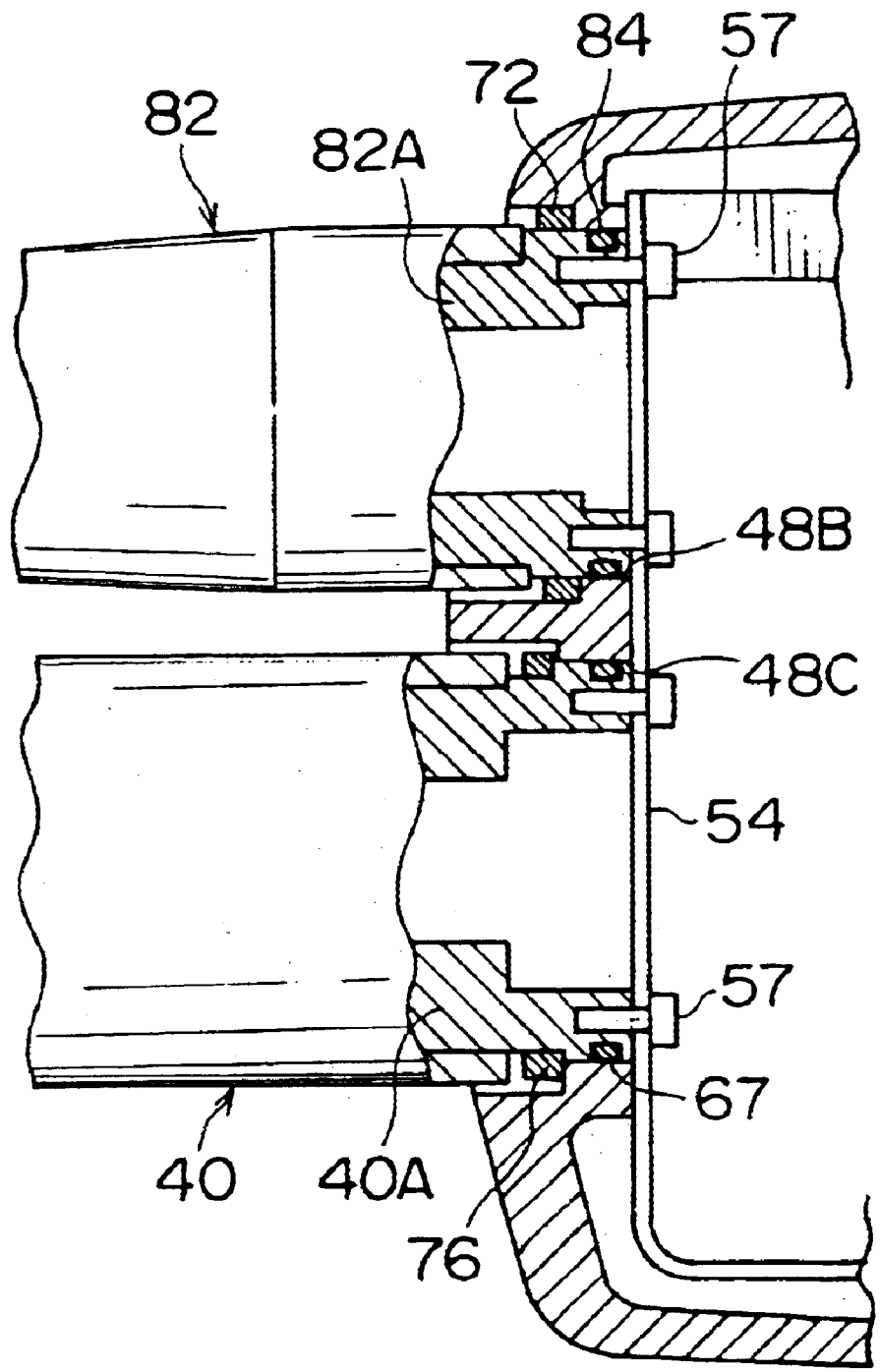
FIG. 7 is a side view for the connector showing a comparative example in which the universal cable has been watertightly sealed with the outer peripheral surface.

In the connector shown in FIG. 7, both a universal cable 82 and a control cable 40 are sealed at the outer peripheral surface. More specifically, the distal end portion 82A of the universal cable 82 is fitted into the mounting hole 48B, and on the outer peripheral surface thereof, there is disposed an O-ring 84. On assembling this connector, the moment when the distal end portion 82A of the universal cable 82 is fitted into the mounting hole 48B, the distal end portion 40A of the control cable 40 must be inserted into the mounting hole 48C. Therefore, since two cables are fitted into the mounting holes 48B, 48C of the case body 48 respectively at the same time, there is a defect that it is low in assembly property. Also, when the fixed positions of those two cables are deviated, the cable cannot be fitted into the mounting hole 48B, 48C, nor the connector can be assembled in some instances.

Figure 8:
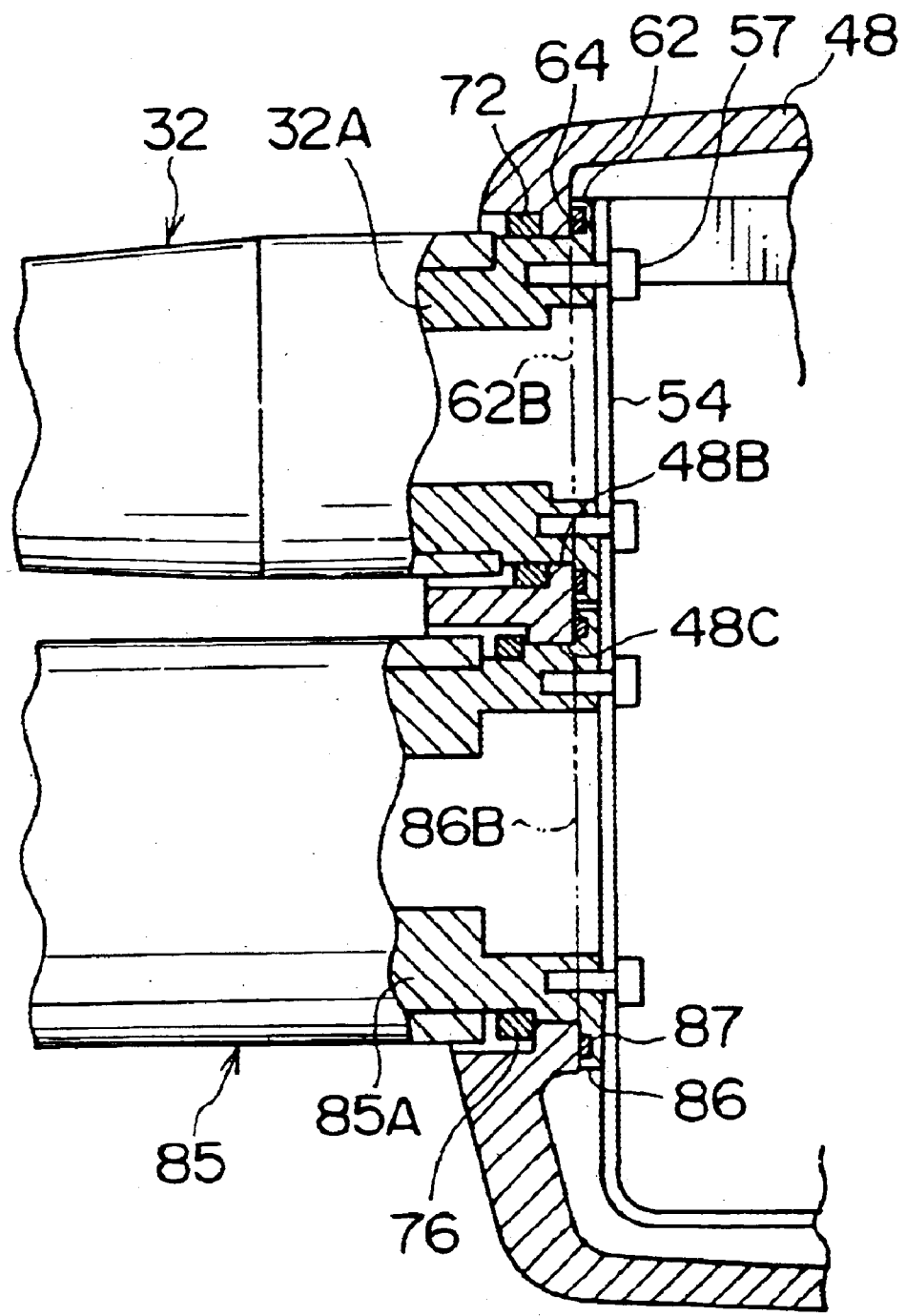
FIG. 8 is a side view for the connector showing a comparative example in which the control cable has been watertightly sealed with a surface orthogonal to the shaft.

On the other hand, in the connector shown in FIG. 8, both a universal cable 32 and a control cable 85 are sealed at a surface orthogonal to the axis of the cable. More specifically, at the distal end portion 85A of the control cable 85, there is formed a flange 86, and the abutting surface 86B of this flange 86 abuts against the case body 48, and the flange 86 and the case body 48 are sealed by an O-ring 87 disposed on the abutting surface 86B. Also, the control cable 85 is formed such that the distal end portion 85A is somewhat smaller than the mounting hole 48C of the case body 48 so that some gap is formed between the distal end portion 85A and the case body 48.

The connector of FIG. 8 can be assembled by easily sliding the case body 48 because both the universal cable 32 and the control cable 85 can be loosely fitted in the mounting holes 48B, 48C of the case body 48.

However, for the connector of FIG. 8 to obtain the watertightness of the case body 48, the abutting surface 62B of the universal cable 32 and the abutting surface 86B of the control cable 85 must be caused to abut against the case body 48 at the same time. Accordingly, very high machining precision is required for the distal end portion 32A of the universal cable 32, the distal end portion 85A of the electric connector 85 and the like, and therefore, there is a defect that the cost is high. Also, when the abutting surface 62B and the abutting surface 86B do not abut against the case body 48 at the same time with a low degree of machining precision, there is a fear that sealing in these places becomes incomplete, and the watertightness of the connector cannot be reliably maintained.

In contrast, the LG connector 34 according to the present embodiment is constructed such that the universal cable 32 is sealed by a surface orthogonal to the shaft thereof and the control cable 40 is sealed by the outer peripheral surface thereof. Accordingly, while the control cable 40 is fitted into the mounting hole 48C to seal the control cable 40 and the case body 48, the case body 48 is further caused to slide on the proximal portion 46 side to cause the abutting surface 62B of the universal cable 32 to abut against the case body 48, whereby the universal cable 32 and the case body 48 can be sealed. In other words, while maintaining the watertightness on the control cable 40 side, the watertightness on the universal cable 32 side can be obtained. Thereby, the watertightness of the LG connector 34 can be reliably held.

Also, on assembling the LG connector 34, the distal end portion 40A of the control cable 40 is inserted into the mounting hole 48C while the distal end portion 32A of the universal cable 32 is loosely fitted in the mounting hole 48B. Accordingly, relative to the control cable 40 side, the case body 48 can be somewhat rocked, and therefore, the control cable 40 and the universal cable 32 can be easily inserted into the mounting holes 48B, 48C respectively. Thereby, the LG connector 34 can be easily assembled.

As described above, in the LG connector 34 according to the present embodiment, the assembly property can be improved without deteriorating the watertightness.

In this respect, in the above described embodiment, both the universal cable 32 and the case body 48 have been sealed by a surface orthogonal to the axis of the universal cable 32, and both the control cable 40 and the case 48 have been sealed by the outer peripheral surface of the control cable 40, but conversely, the universal cable 32 may be sealed together with the case body 48 by the outer peripheral surface thereof, and the control cable 40 may be sealed together with the case body 48 by a surface orthogonal to the axis thereof.

Figure 9:
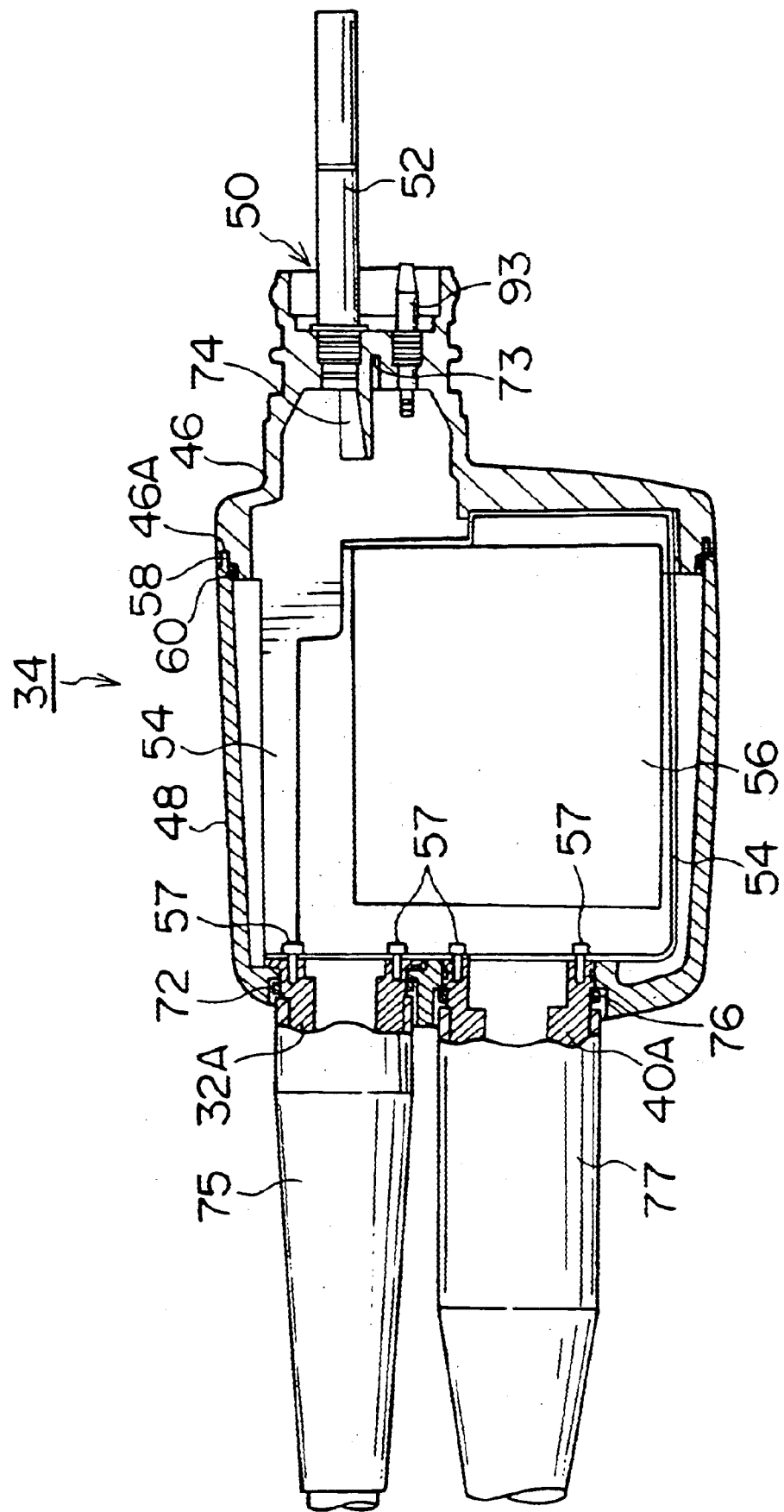
FIG. 9 is a side view showing the LG connector.
Figure 10:
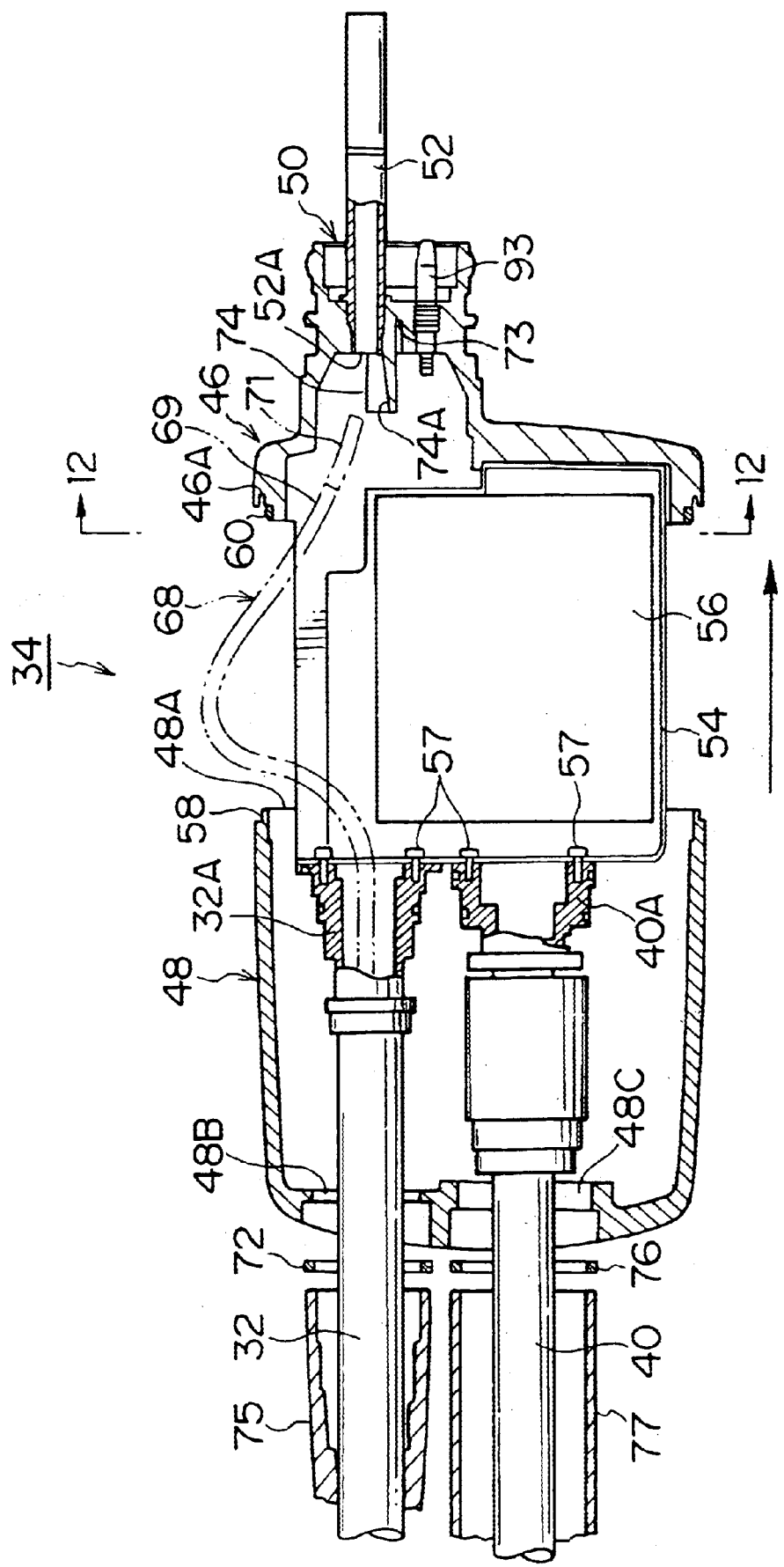
FIG. 10 is an assembly view showing the LG connector.
Figure 11:
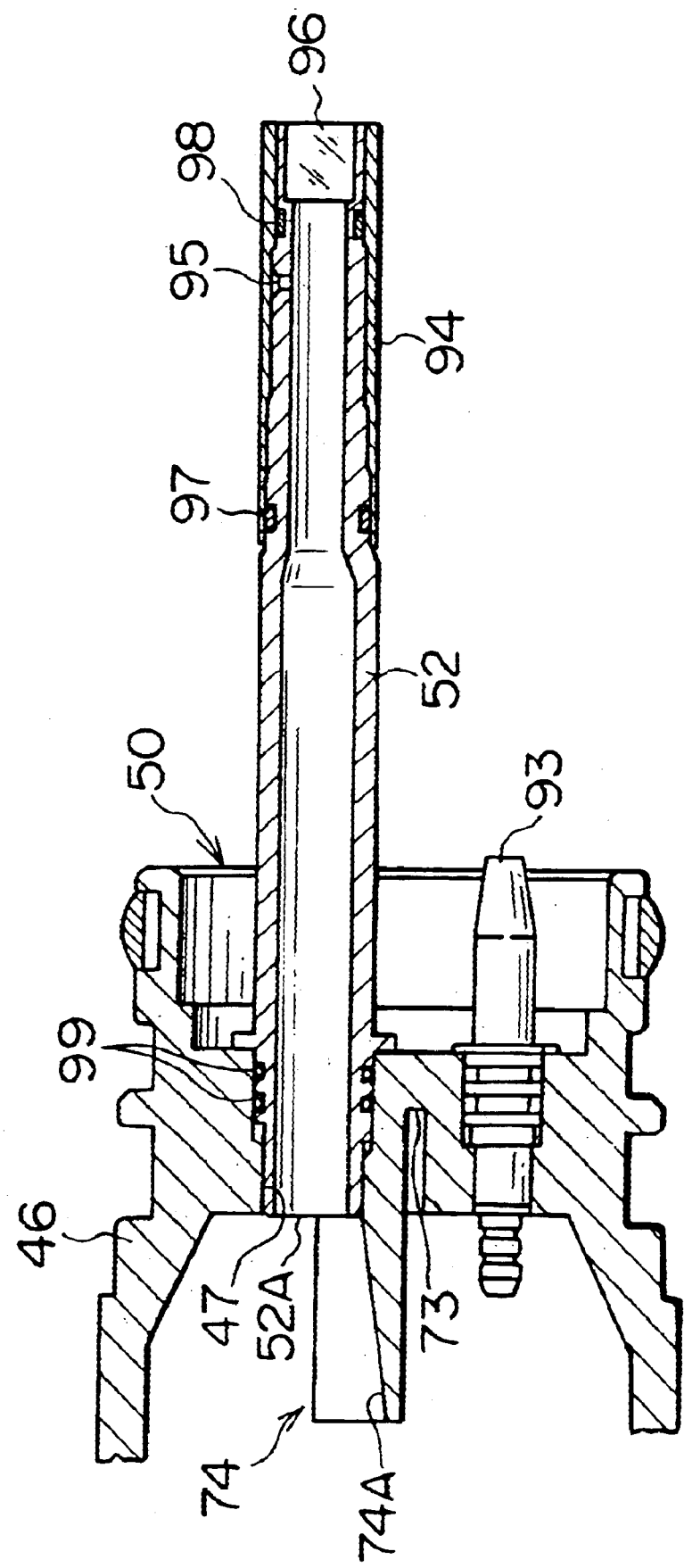
FIG. 11 is a side sectional view showing the guide member.

As shown in FIGS. 9 and 10, the light guide bar 52 is projectedly provided on a joint 50 of the proximal portion 46. The light guide bar 52 is formed in a cylindrical shape as shown in FIG. 11, and threadedly engaged with a threaded hole 47 of the proximal portion 46. Also, the light guide bar 52 has an LG window glass 96 disposed in an air-tight state inside the distal end portion, and a sleeve 94 detachably fitted over the outside of the distal end portion. Within the light guide bar 52, the light guide 68 is inserted as shown in FIG. 10. In the light guide 68, extra-fine optical fibers are covered with a silicon tube 69, and its distal end portion is fixed using a tip base 71. A light guide 68 which has been inserted to a predetermined position has the tip base 71 which is fixed by means of a set screw 95 shown in FIG. 11.

Figure 12:
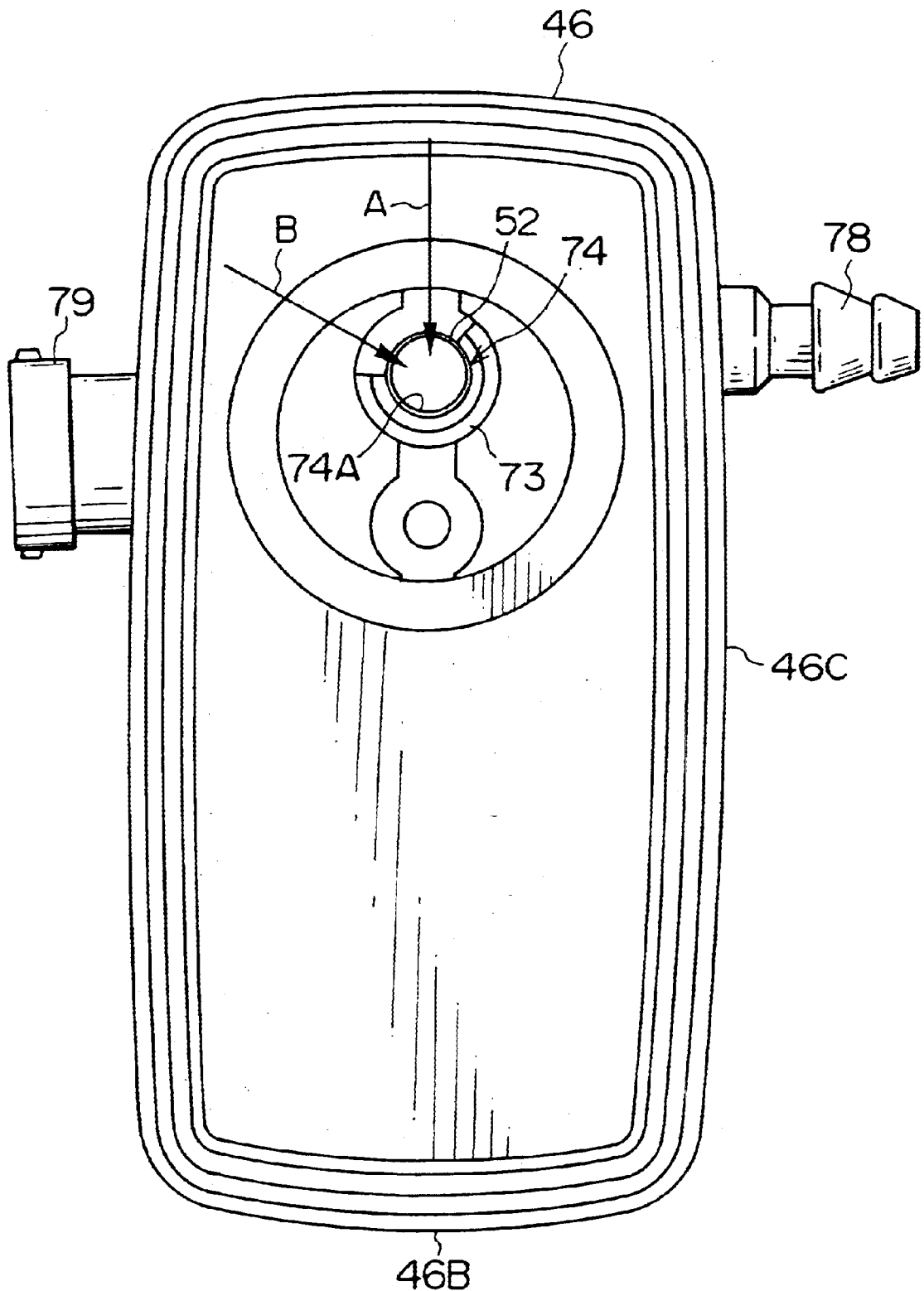
FIG. 12 is an arrow view taken along line 12—12 of FIG. 10.
Figure 13A:
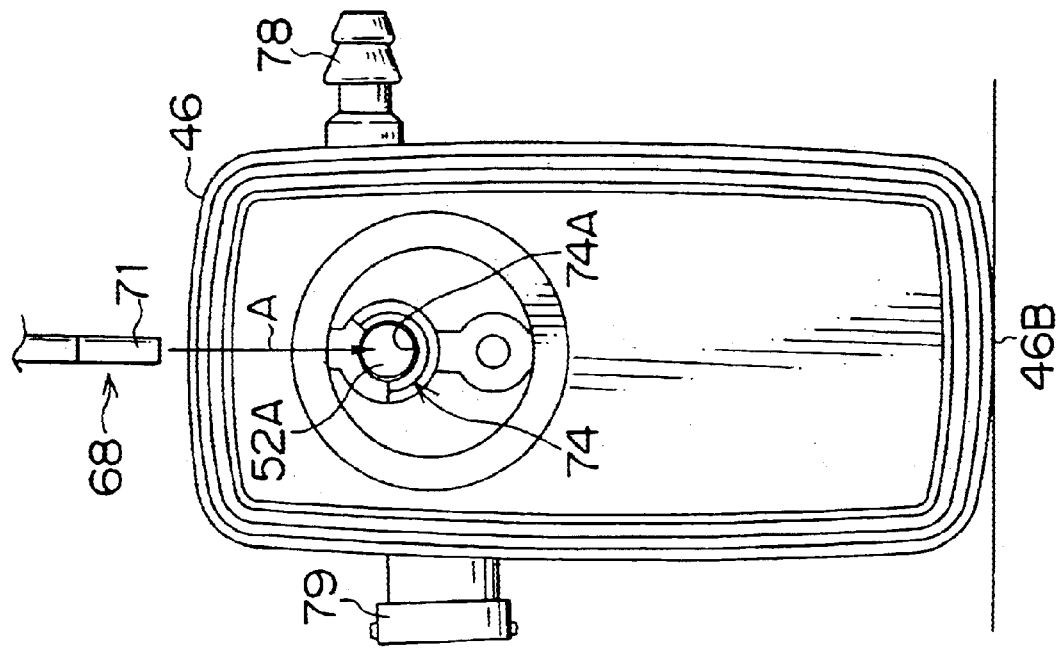
FIGS. 13(A) and 13(B) are explanatory views showing inserted state of the light guide.
Figure 13B:
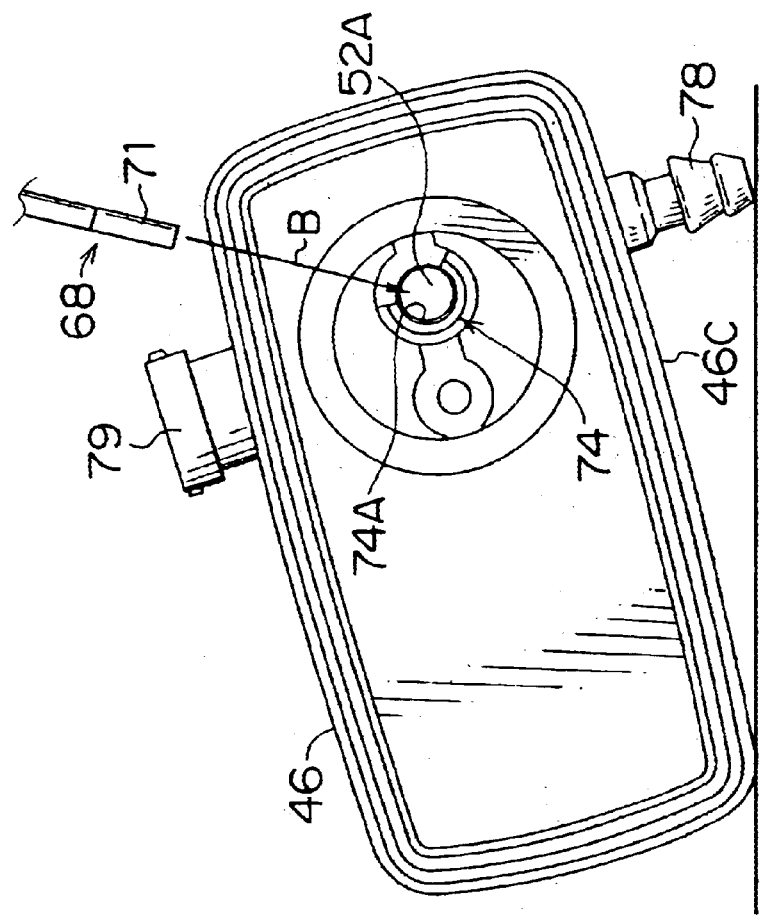
Figure 14:
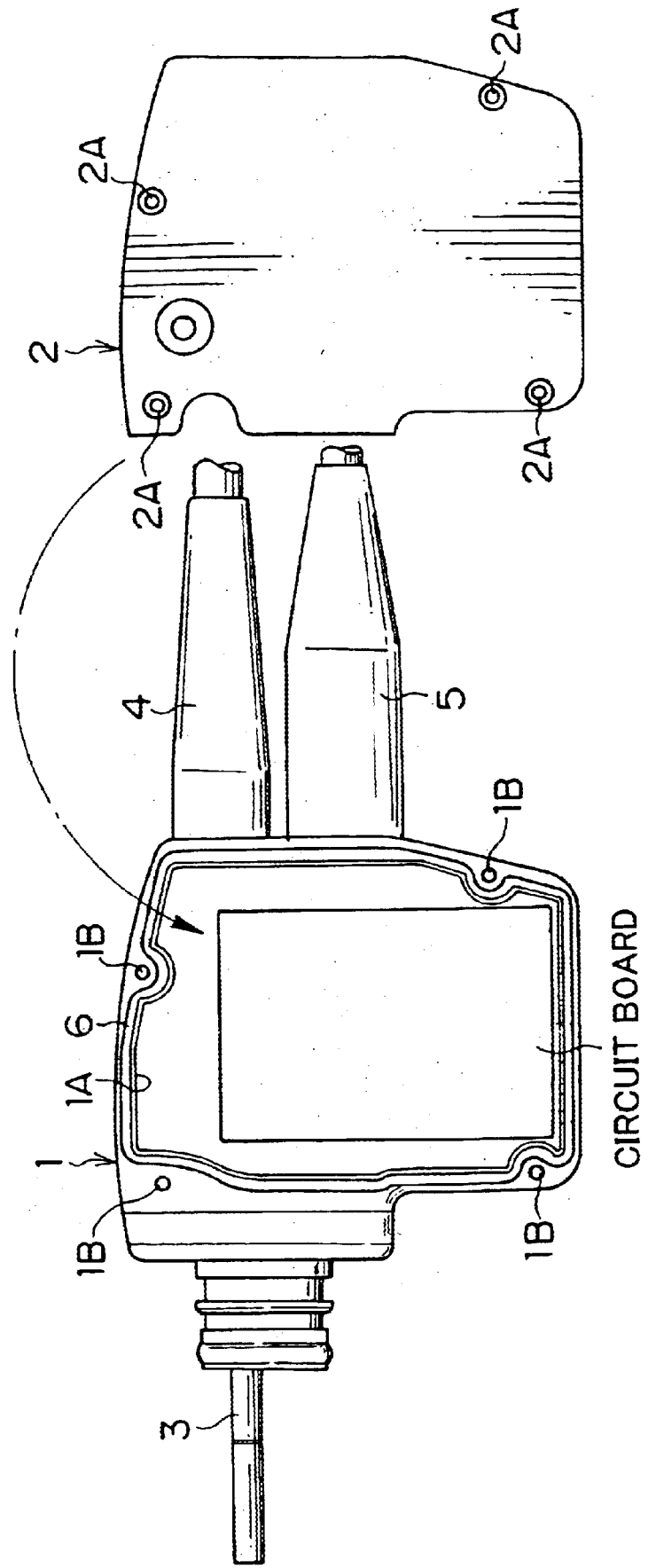
FIG. 14 is a side view showing a conventional connector for the endoscope.
Figure 15:
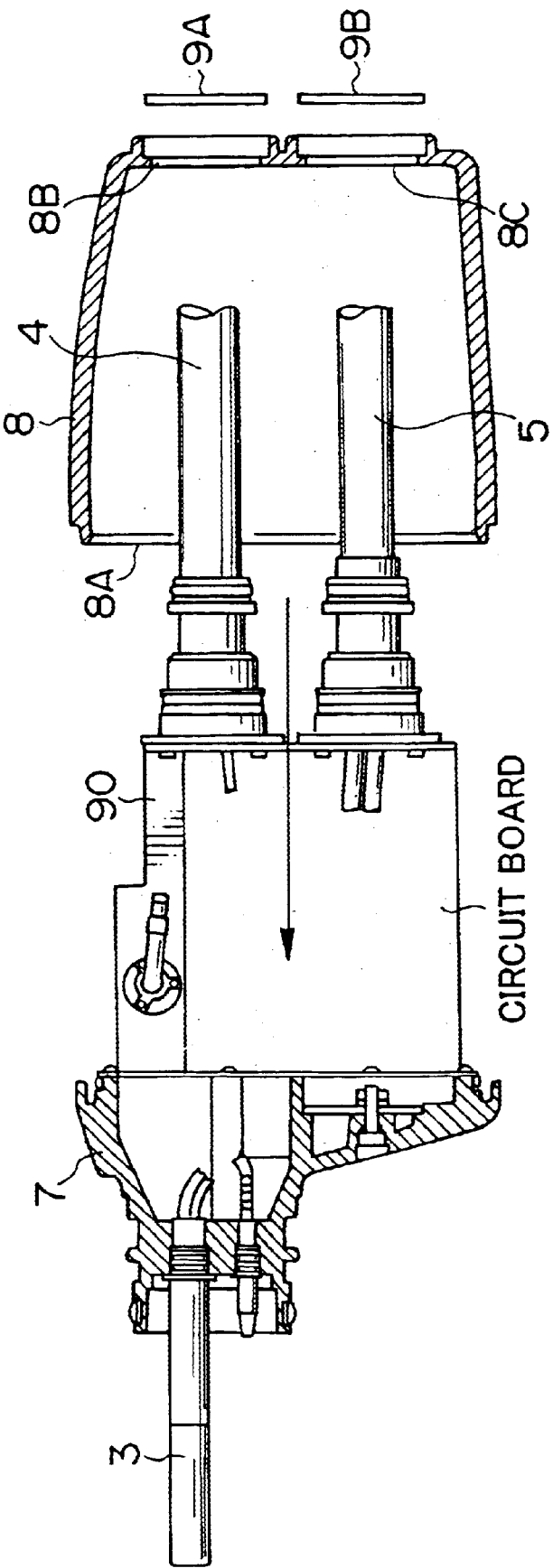
FIG. 15 is a side view showing the conventional connector for the endoscope.

An insertion port 52A of the light guide bar 52 is provided with a guide member 74 which guides the light guide 68 to the light guide bar 52. The guide member 74 is integrally formed together with the proximal portion 46, and is projectedly provided on the inner surface of the proximal portion 46. Also, the guide member 74 is formed with a circular arc-shaped groove 74A. The groove 74A is formed such that the proximal portion has the substantially same diameter as the insertion port 52A and that the diameter becomes gradually larger toward the projecting end side. Also, the groove 74A is opened on the side of a direction of insertion of the light guide 68. Since the light guide 68 is inserted toward the guide member 74 from a range enclosed by a direction from right above toward right under (direction indicated by an arrow A) and a direction from the upper left toward the lower right (direction indicated by an arrow B) as shown in FIG. 12, the groove 74A is of a shape (specifically, shape opened about 135° clockwise from horizontal left direction) in which the upper portion and the left upper portion have been continuously opened. Accordingly, even when the light guide 68 has been inserted from the direction indicated by the arrow A with the surface 46B of the proximal portion 46 down as shown in FIG. 13(A), and even when the light guide 68 has been inserted from the direction indicated by an arrow B with the surface 46C of the proximal portion 46 down as shown in FIG. 13(B), the light guide 68 can be guided to the insertion port 52A by means of the groove 74A of the guide member 74. In this respect, since on the surface 46C of the proximal portion 46, a suction piping tool 78 is projectedly provided, the proximal portion 46 is obliquely arranged when the surface 46C is turned downward.

On the side of the outer periphery of the guide member 74, there has been formed a receding ridge portion 73, and the guide member 74 has been constructed so as to easily resiliently deform.

In this respect, a reference numeral 93 in FIG. 11 denotes an air piping tool, and is connected to the connector 36 on the light source device 14 side to thereby supply air. Also, reference numerals 97 and 88 denote an O-ring which seals both the light guide bar 52 and the sleeve 94, and a reference numeral 99 denotes an O-ring which seals both the light guide bar 52 and the proximal portion 46. A reference numeral 78 in FIG. 12 denotes a suction piping tool, to which a tube from the suction apparatus is connected. A reference numeral 79 denotes an air/water piping tool, to which a tube from a water supply tank is connected.

Next, the description will be made of an operation of the LG connector 34 constructed as described above.

On installing the light guide 68, the distal end of the light guide 68 is first drawn out of the universal cable 32 as shown in FIG. 10. Thus, the distal end of the light guide 68 drawn out is guided by the guide member 74 to cause it to be inserted from the insertion port 52A of the light guide bar 52. At this time, since the groove 74A of the guide member 74 on the projecting end side has been formed large, the light guide 68 can be easily inserted into the groove 74A. Also, since the groove 74A has been gradually formed smaller toward the proximal end portion side, the distal end of the light guide 68 can be guided to the insertion port 52A only by pressing in the light guide 68 along the groove 74A. In this respect, even if the distal end of the light guide 68 strikes against the guide member 74, there is no possibility that the light guide 68 is damaged because the guide member 74 resiliently deforms.

After the light guide 68 is inserted to a predetermined position, the distal end of the light guide 68 is fixed by means of set screw 95. A sleeve 94 is mounted onto the distal end of the light guide bar 52, whereby the assembly operation of the light guide 68 is completed.

According to the LG connector 34 of the present embodiment as described above, since the proximal portion 46 has been provided with the guide member 74, the light guide 68 can be smoothly inserted into the light guide bar 52. Accordingly, the light guide 68 can be prevented from being damaged due to a great load.

Also, since with the provision of the receding ridge portion 73 on the side of the outer periphery of the guide member 74, the guide member 74 has been constructed so as to easily resiliently deform, even if the distal end of the light guide 68 strikes against the guide member 74, the guide member 74 is capable of absorbing, by means of the resilient deformation, a force to which it is subjected. Therefore, the light guide 68 can be prevented from being damaged.

Also, in the guide member 74 according to the present embodiment, even if the operation is performed with the surface 46B of the proximal portion 46 down, or even if the operation is performed with the surface 46C down, the light guide 68 can be smoothly inserted into the light guide bar 52.

In this respect, the shape of the guide member 74 is not limited to the above described embodiments, but alternatively, the shape may be a shape which is capable of guiding the distal end of the light guide 68 to the insertion port 52A of the light guide bar 52.

Also, in the above described embodiments, the guide member 74 has been formed integrally with the proximal portion 46, and the present invention is not limited thereto, but a guide member formed discretely from the proximal portion 46 may be detachably mounted to the proximal portion 46. In this case, after the light guide 68 is inserted into the light guide bar 52, the guide member is removed, whereby space of the guide member thus removed can be effectively utilized.

As described above, according to the connector device for an endoscope of the present invention, the structure has been arranged such that one of the first cable and the second cable is sealed together with the case body by the outer peripheral surface of the cable, and the other cable is sealed together with the case body by the surface orthogonal to the axis thereof, and therefore, it is possible to obtain the watertightness and to improve the assembly property.

In addition, since there has been provided the guide member which guides the light guide to the light guide bar, it is possible to easily install without damaging the light guide.

It should be understood, however, that there is no intention to limit the invention to the specific forms disclosed, but on the contrary, the invention is to cover all modifications, alternate constructions and equivalents falling within the spirit and scope of the invention as expressed in the appended claims.

What is claimed is:

1. A connector device for an endoscope, comprising:
   a first cable to be connected to an endoscope on-hand operating unit and a second cable to be connected to a controller which processes a signal, the first cable and the second cable are coupled on a first side of a proximal portion of the connector device;
   a light guide bar to be coupled to a light source device positioned on a second side of the proximal portion of the connector device;
   the first side of the proximal portion is watertightly sealed with a case body having an insertion port of the first cable and an insertion port of the second cable;
   the case body and at least one of the first cable and the second cable are sealed by a first sealing member provided on an outer peripheral surface of the at least one of the first cable and second;
   the case body and at least one of the first cable and the second cable are sealed by a second sealing member provided on a surface orthogonal to an axis of the at least one of the first cable and the second cable;
   a distal end portion of the second cable includes at least one flange with an abutting surface which abuts the case body, the at least one flange and the case body are sealed by an O-ring disposed on the abutting surface; and
   wherein the distal end portion of the second cable is smaller than a mounting hole of the case body to form a gap between the distal end portion and the case body.

2. The connector device for an endoscope according to claim 1,
   wherein a guide member is configured to guide a distal end of the light guide to an insertion portion of the guide bar.

3. The connector device for an endoscope according to claim 1, wherein a guide member is integrally connected to the proximal portion.

4. The connector device for an endoscope according to claim 1, wherein a guide member is detachably mounted to the proximal portion.

5. The connector device for an endoscope according to claim 1, wherein a guide member is projectedly provided on an inner surface of the proximal portion.

6. The connector device for an endoscope according to claim 1, wherein a guide member is formed with a groove.

7. The connector device for an endoscope according to claim 6, wherein a diameter of the groove of the guide member increases toward a projecting end side.

8. The connector device for an endoscope according to claim 1, wherein a guide member is formed with a circular arc-shaped groove.

9. The connector device for an endoscope according to claim 1, wherein the light bar is in close proximity with a guide member.

10. The connector device for an endoscope according to claim 1, including guide means for guiding a distal end of the light guide to an insertion point of the guide bar.

11. A connector device for an endoscope, comprising:

a first cable connected to an endoscope on-hand operating unit and a second cable connected to a controller which processes a signal, the first cable and the second cable are coupled on a first side of a proximal portion of the connector device;

a light guide bar coupled to a light source device positioned on a second side of the proximal portion of the connector device;

the first side of the proximal portion is watertightly sealed with a case body having an insertion port of the first cable and an insertion port of the second cable;

the case body and at least one of the first cable and the second cable are sealed by a first sealing member provided on an outer peripheral surface of the at least one of the first cable and second;

the case body and at least one of the first cable and the second cable are sealed by a second sealing member provided on a surface orthogonal to an axis of the at least one of the first cable and the second cable;

wherein a guide member is configured to guide a distal end of the light guide to an insertion portion of the guide bar; and wherein guide bar member includes a groove with a diameter that increases towards a projecting side.

12. The connector device for an endoscope according to claim 11, wherein a guide member is integrally connected to the proximal portion.

13. The connector device for an endoscope according to claim 11, wherein a guide member is detachably mounted to the proximal portion.

14. The connector device for an endoscope according to claim 11, wherein a guide member is projectedly provided on an inner surface of the proximal portion.

15. The connector device for an endoscope according to claim 11, wherein a guide member is formed with a circular arc-shaped groove.

16. The connector device for an endoscope according to claim 11, wherein the light bar is in close proximity with a guide member.

* * * * *